United States Patent [19]

Kerscher et al.

[11] Patent Number: 4,892,815

[45] Date of Patent: Jan. 9, 1990

[54] PROCESS AND REAGENT FOR THE SPECIFIC DETERMINATION OF THE CHOLESTEROL OF THE HDL FRACTION

[75] Inventors: Lorenz Kerscher, Penzberg; Brigitte Pautz; Gisela Trunk, both of Herrsching; Joachim Ziegenhorn, Starnberg, all of Fed. Rep. of Germany

[73] Assignee: Boehringer Mannheim GmbH, Mannheim-Waldhof, Fed. Rep. of Germany

[21] Appl. No.: 107,467

[22] Filed: Oct. 6, 1987

[30] Foreign Application Priority Data

Oct. 29, 1986 [DE] Fed. Rep. of Germany ....... 3636851

[51] Int. Cl.$^4$ .................. C12Q 1/60 A; G01N 33/68; G01N 33/92 B
[52] U.S. Cl. ........................................ 435/7; 435/11; 435/19; 435/25; 435/28; 435/805; 436/71; 436/810; 436/824
[58] Field of Search ................... 435/7, 11, 19, 25, 28, 435/805; 436/810, 824, 71

[56] References Cited

U.S. PATENT DOCUMENTS

| | | | |
|---|---|---|---|
| 4,164,448 | 8/1979 | Röeschlau et al. | 435/11 |
| 4,275,151 | 6/1981 | Esders et al. | 435/11 |
| 4,312,834 | 1/1982 | Vogel et al. | 435/11 X |
| 4,409,326 | 10/1983 | Modrovich | 435/11 |
| 4,544,630 | 10/1985 | Ziegenhorn et al. | 435/11 |
| 4,746,605 | 5/1988 | Kerscher et al. | 435/11 X |

FOREIGN PATENT DOCUMENTS 3533288 3/1987 Fed. Rep. of Germany ........ 435/11
8604144 7/1986 PCT Int'l Appl. .................... 435/7

*Primary Examiner*—Robert J. Warden
*Assistant Examiner*—Carol A. Spiegel
*Attorney, Agent, or Firm*—Felfe & Lynch

[57] ABSTRACT

The present invention provides a process for the specific determination of the cholesterol of the HDL fraction in the presence of the LDL fraction of serum lipoproteins. Pancreatic cholesterol esterase is used to liberate cholesterol, and the liberated cholesterol then reacts with cholesterol oxidase and oxygen to form hydrogen peroxide. The kinetics of either of hydrogen peroxide formation or oxygen consumption is measured within 2 to 15 minutes after the start of the reaction between cholesterol and the oxidase. The temperature is maintained within a range of 20° C., during a predetermined time interval. Specific concentrations of reactants are maintained in the reaction solution, i.e., from 0.05 to 30 U/ml pancreatic cholesterol esterase; from 0.1 to 50 U/ml cholesterol oxidase; from 1.0 to 20 mMole/liter of a tenside of the bile acid group, and 0.1 to 10 g/liter of a non-ionic detergent. The pH is kept within a range of 5 to 9. In addition, a reagent is provided which is used for specific determination of HDL fraction cholesterol in the presence of the LDL fraction of serum lipoproteins. The reagent contains pancreatic esterase (0.05 to 30 U/ml); cholesterol oxidase (0.1 to 50 U/ml) a tenside of the bile acid grop (1.5 to 8 mMole/liter) and a non-ionic detergent (0.1 to 10 g/liter), all concentrations referring to the dilution used in the test. The reagent also contains a buffer at a pH of from 5 to 9, and a system for photometric determination of hydrogen peroxide.

17 Claims, 5 Drawing Sheets

PROCESS AND REAGENT FOR THE SPECIFIC DETERMINATION OF THE CHOLESTEROL OF THE HDL FRACTION

The present invention is concerned with a process and a reagent for the specific determination of the cholesterol of the HDL fraction in the presence of the LDL fraction of the lipoproteins of the serum by the action of cholesterol esterase for the liberation of the cholesterol and oxidation of the liberated cholesterol with cholesterol oxidase and oxygen with the formation of hydrogen peroxide and kinetic measurement of the hydrogen peroxide formation or of the oxygen consumption.

The determination of total cholesterol as well as of the individual cholesterol-containing lipid fractions in the serum is of great importance in the clinical laboratory. Hypercholesterolaemia and hypertriglyceridaemia favour the formation of an atherosclerosis and of cardiac infarct. Therefore, an individual's coronary risk can be determined via a determination of cholesterol and triglycerides in the serum. Even better predictions can be made when, in addition, pathological displacements in the lipoprotein pattern can be determined. The proportion of the individual lipid fractions of the total cholesterol permits predictions regarding the risk of infarct, whereby, on the one hand, extensive clinical studies have shown that an increased total serum cholesterol level leads to an increased risk of cardiac infarct, whereas, on the other hand, there is an inverse relationship between the serum HDL cholesterol and the danger of atherosclerotic blood vessel changes.

The lipoproteins of the serum can be divided into four groups: chylomicrons, pre-β-lipoproteins (also called very low density lipoproteins or VLDL), β-lipoproteins (also called low density lipoproteins or LDL) and α-lipoprotein (also called high density lipoprotein or HDL).

For the determination of the serum total cholesterol, since about 15 years there have been available simple but, nevertheless, very exact, completely enzymatic analysis processes which can be carried out not only manually but also equally well with automated analysis systems without any sample pretreatment, these processes usually being carried out according to the following reaction sequence:

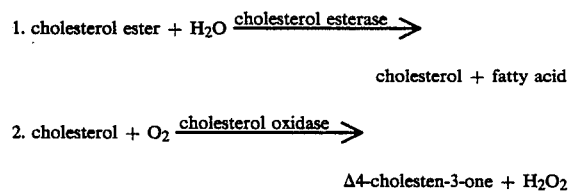

The hydrogen peroxide formed can then be measured, preferably colorimetrically but possibly kinetically.

It is also already known to carry out determination of the HDL cholesterol in serum after separating off the other cholesterol-containing lipoproteins. The separation of these lipoproteins can take place by ultracentrifuging, electrophoresis or diverse precipitation methods, such as immune precipitation, precipitation with phosphotungstic acid/magnesium ions, dextran sulphate/magnesium ions or heparin/magnesium ions or with polyethylene glycol. All these processes are laborious and require several reaction steps and a relatively great expenditure of time.

Furthermore, from U.S. Pat. No. 4,544,630, it is also known that the proportion of the cholesterol content of the LDL fraction can be determined directly. This determination is based on the recognition that, under certain conditions, the reaction velocity of the cholesterol content of the LDL fraction depends linearly upon the concentration thereof and that, in the case of a kinetic measurement, the measurement value thereby obtained is directly proportional to the LDL cholesterol concentration in the reaction batch. This process is very well suited for the determination of LDL but a determination of the HDL content therewith is, however, not possible.

It is an object of the present invention to provide a process and a reagent which permits the determination of HDL in serum with simple agents and in one step. In particular, there is provided a process with the help of which the total cholesterol can also be determined simultaneously.

Thus, according to the present invention, there is provided a process for the specific determination of the cholesterol of the HDL fraction in the presence of the LDL fraction of the lipoproteins of the serum by the action of cholesterol esterase for the liberation of the cholesterol and oxidation of the liberated cholesterol with cholesterol oxidase and oxygen with the formation of hydrogen peroxide and kinetic measurement of the hydrogen peroxide formation or of the oxygen consumption, wherein the measurement is carried out within 2 to 15 minutes after the start of the oxidase reaction at a temperature of from 20 to 40° C. During a predetermined time interval and during the measurement there is maintained in the reaction solution a cholesterol esterase concentration of 0.05 to 30 U/ml., a cholesterol oxidase concentration of 0.1 to 50 U/ml., a concentration of a tenside of the bile acid group of 1.0 to 20 mMole/liter, a concentration of a non-ionic detergent of 0.1 to 10 g./liter and a pH value of 5 to 9.

Surprisingly, we have ascertained that the reaction of the cholesterol of the serum lipoproteins by means of cholesterol esterase and cholesterol oxidase in the presence of appropriate detergent combinations proceeds in two phases. The reaction proceeds first with a velocity which is dependent upon the LDL cholesterol concentration but independently of the HDL concentration. In the further course of the reaction, it is then dependent upon a time point, dependent upon the reaction conditions, of the reaction velocity of the HDL cholesterol concentration. Thus, the reaction of the HDL fraction takes place with a time delay. In the case of appropriate choice of the reaction conditions, the HDL reaction can be observed at a time point at which the LDL cholesterol has already been substantially reacted. The extinction change in an appropriately chosen time interval is then proportional to the HDL cholesterol concentration. In this way, it is possible, by means of a simple process, to determine the HDL directly in the presence of other cholesterol-containing lipid fractions.

It is important for the process according to the present invention that the reaction conditions are so adjusted that the HDL reaction takes place at a favourable time point.

In the case of the process according to the present invention, by the addition of cholesterol esterase to the reaction solution, there is first brought about the liberation of the cholesterol. The cholesterol esterase can be obtained from various organisms, for example microorganisms or animal tissues. Microbial cholesterol esterase is obtained, for example, from Pseudomonas or Candida. However, cholesterol esterase from pancreas, for example bovine or porcine pancreas, has proved to be especially suitable. The concentration of the cholesterol esterase in the reaction solution is from 0.05 to 30 U/ml., preferably from 0.05 to 10 U/ml. and more preferably from 0.05 to 1 U/ml.

The measurement unit U for cholesterol esterase is based upon the following definition: 1 U is the amount of enzyme which reacts 1 μmole cholesterol linoleate per minute at 37° C., the reaction mixture containing, besides the cholesterol esterase, the following components:

0.2 mole/liter potassium phosphate buffer (pH 7.0)
0.15 mole/liter sodium chloride
4 g./liter sodium cholate
16 g./liter THESTI ®(non-ionic detergent)
2 g./liter phenol
0.3 g./liter 4-aminoantipyrine
20 U/ml. peroxidase from horseradish
0.2 U/ml. cholesterol oxidase from Nocardia erythrooolis
0.45 g./liter cholesteryl linoleate.

The liberated cholesterol is then oxidised with cholesterol oxidase to give cholestenone and hydrogen peroxide. The cholesterol oxidase can also be obtained from various organisms. A cholesterol oxidase is preferably used which has obtained from Brevibacterium, Nocardia or Streotomyces. The concentration of the cholesterol oxidase is from 0.1 to 50 U/ml., preferably from 1 to 30 U/ml. and more preferably from 5 to 25 U/ml.

The measurement unit U for cholesterol oxidase is based upon the following definition: 1 U is the amount of enzyme which reacts 1 μmole cholesterol per minute at 25° C., the reaction mixture containing, besides the enzyme, the following components:

0.47 mole/liter potassium phosphate buffer (pH 7.5)
8 g./liter THESIT ®
2.5 g./liter n-propanol
0.125 g./liter cholesterol Furthermore, it is important for the process according to the present invention that a tenside of the bile acid group is present in the reaction solution. This tenside is present in a concentration of from 1.0 to 20 mMole/liter and preferably of from 1.5 to 8 mMole/liter. Tensides of the bile acid group are known, derivatives of cholic acid preferably being used and sodium cholate being especially preferred.

A non-ionic detergent is also present in the reaction solution. The concentration of this non-ionic detergent is from 0.1 to 10 g./liter and preferably from 0.4 to 4 g./liter. As non-ionic detergent it is preferred to use a detergent which contains polyethylene oxide groups. Detergents based on sugars can also be used. Examples of non-ionic detergents include alkyl- and aralkyl-polyethylene oxide ethers, for example n-dodecyl polyethylene glycol ethers, isotridecanol polyethylene oxide ethers and isooctylphenyl polyethylene oxide ethers.

In a preferred embodiment of the process according to the present invention, the non-ionic detergent is added after the addition of the oxidase but 1 to 14 minutes before the measurement.

The pH value of the reaction solution is in the range of from 5 to 9. For the adjustment of the necessary pH value, there are used buffers which are effective in this range. Although the nature of the buffer substance used is not critical, it is preferred to use TRIS/HCl buffer and especially phosphate buffer.

The process according to the present invention is carried out at a temperature of from 20 to 40° C., a temperature of from 25 to 37° C. being especially preferred.

In the case of maintenance of the parameters which are important for the present invention, the measurement of the cholesterol of the HDL fraction takes place in a time range of from 2 to 15 minutes after the start of the oxidase reaction, the measurement preferably being carried out in the time range of from 3 to 10 minutes after the start of the oxidase reaction.

If the measurement of the hydrogen peroxide must take place under less favourable reaction and measurement conditions, the reaction of residues of the LDL fraction can still take place within the time interval chosen for the measurement and could thus disturb the measurement of the HDL fraction. In order to avoid this disturbance, in a further embodiment of the process according to the present invention, such a loss of specificity is prevented by the addition of anti-LDL antibodies. This antiserum brings the reaction of the LDL to an end at an early stage. For this purpose, there can be used known anti-LDL antibodies or also anti-apolipoprotein-B antibodies alone or in mixtures. These antibodies are preferably present in a concentration of from $10^{-6}$ to $10^{-4}$ mMole/liter as defatted γ-globulin or IgG preparation.

As already mentioned hereinbefore, in the case of the process according to the present invention, there first takes place the liberation of the cholesterol present in the LDL fraction so that the measurement signal is first proportional to the cholesterol content of the LDL fraction. Therefore, with the help of the process according to the present invention, from one test batch it is possible to determine not only LDL cholesterol but also HDL cholesterol. Since the reaction velocity is first LDL-dependent and later HDL-dependent, within each reaction phase there can be chosen the particularly most favourable time interval for the measurement of the LDL- and HDL-dependent extinction changes. For this purpose, within the first minute after the start of the oxidase reaction, the hydrogen peroxide formation is determined kinetically as a measure of the cholesterol bound in the LDL fraction of the serum. Subsequently, in a time interval of from 2 to 15 minutes after the start of the oxidase reaction, the hydrogen peroxide formation is determined kinetically as a measure for the cholesterol bound in the HDL fraction of the serum Furthermore, according to a favourable embodiment of the process according to the present invention, it is possible, after measurement of the HDL cholesterol, so to increase the concentration of cholesterol esterase by the addition of a second reagent solution that the reaction of the total cholesterol content takes place completely within a short time. The total amount of cholesterol in the sample is then determined. For this purpose, it suffices additionally to add cholesterol esterase and optionally cholesterol oxidase and/or tenside in high concentrations, i.e. above the amount previously described for the HDL cholesterol determination, as soon as the HDL determined is ended.

In the same way, however, simply the addition of a sufficient amount of an appropriate reagent according to the prior art can take place for the rapid and complete reaction of the total cholesterol.

Thus, with the process according to the present invention, it is possible to determine in a sample in parallel the proportion of LDL fraction and HDL fraction, as well as the total cholesterol.

The determination of free cholesterol by means of cholesterol oxidase with the formation of hydrogen peroxide and cholestenone and the kinetic determination of the change of a reaction component of this oxidation reaction is known, for example, from U.S. Pat. No. 4,229,527. Hydrogen peroxide thereby formed is preferably determined with the use of known colorimetric methods of hydrogen peroxide determination. A typical method of determining hydrogen peroxide, which is very well suited for the process according to the present invention, depends upon the colour reaction of phenol or of a phenol derivative with 4-aminoantipyrine or a derivative thereof in the presence of peroxidase. These determinations are well known and do not need to be described here in detail.

The present invention also provides a reagent for the specific determination of the cholesterol of the HDL fraction in the presence of the LDL fraction of the lipoproteins of the serum, which contains cholesterol esterase, cholesterol oxidase, a tenside of the bile acid group, non-ionic detergent, buffer (pH 5 to 9) and a system for the photometric determination of hydrogen peroxide, which contains the cholesterol esterase in a concentration of 0.05 to 30 U/ml., the cholesterol oxidase in a concentration of 0.1 to 50 U/ml., the tenside of the bile acid group in a concentration of 1.0 to 20 mMole/liter and the non-ionic detergent in a concentration of 0.1 to 10 g./liter, in each case referred to the dilution used in the test.

For carrying out the process according to the present invention in an automatic analyzer, the individual reaction components can also be impregnated into or on to a carrier material. As carrier material, there can be used an absorbent, swellable or film-forming material, for example a carrier material known for test strips, such as paper or similar fleece materials, for example tea bag paper. The reaction components can thereby be distributed on several carriers which are in contact with one another.

In a preferred embodiment, the reagent according to the present invention also contains antibodies against LDL and/or apolipoprotein B.

The present invention makes it possible to determine directly the cholesterol contained in HDL without previous separation of the other lipoprotein fractions. Furthermore, it is possible simultaneously also to determine the cholesterol contained in the LDL fraction and the total cholesterol contained in the serum. The process is easy to carry out and can be automated.

The following Examples are given for the purpose of illustrating the present invention, reference being made to the accompanying drawings, in which:

FIG. 1 shows the course of reaction with samples of different HDL cholesterol concentration with a constant LDL cholesterol concentration of 84 mg./dl.; HDL cholesterol in curve 1 = 65.6 mg./dl.; in curve 2 = 56.5 mg./dl.; in curve 3 = 47.4 mg./dl.; in curve 4 = 38.3 mg./dl.; and in curve 5 = 29.2 mg./dl.

EXAMPLE 1

Two human sera with the same content of LDL cholesterol but with a different content of HDL cholesterol are mixed in different ratios so that there is obtained a series of samples which contain increasing amounts of HDL cholesterol with a constant LDL cholesterol content. 0.02 ml. amounts of these samples are each incubated at 30° C with 2.0 ml. of a reagent of the following composition:

0.1 M potassium phosphate buffer (pH 6.7)
8.6 mM tribromohydroxybenzoic acid
1,6 mM 4-aminoantipyrine
3 mM sodium cholate
0.1% polyethylene glycol (M.W. 6000)
0.1% THESIT ®
1 U/ml. cholesterol esterase from pig pancreas
1 U/ml. cholesterol oxidase from Nocardia
2.5 U/ml. peroxidase.

Figure 1:
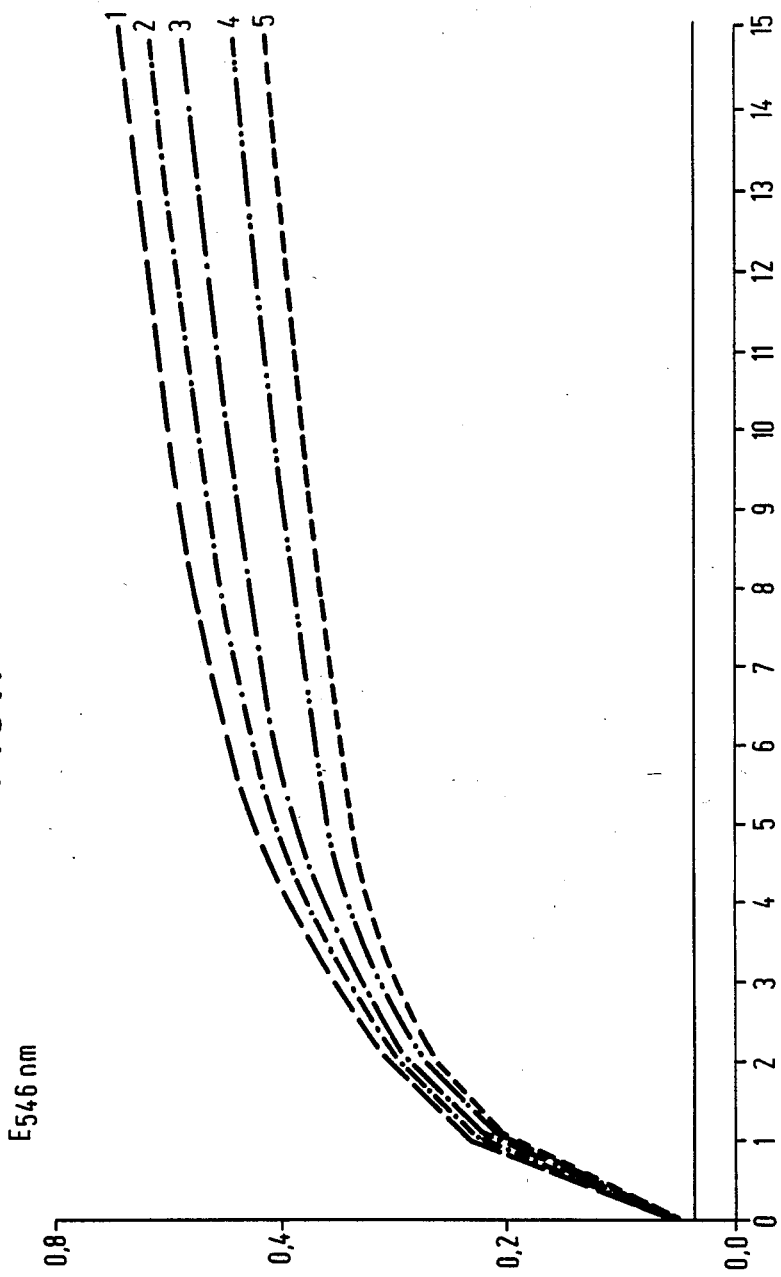
Figure 2:
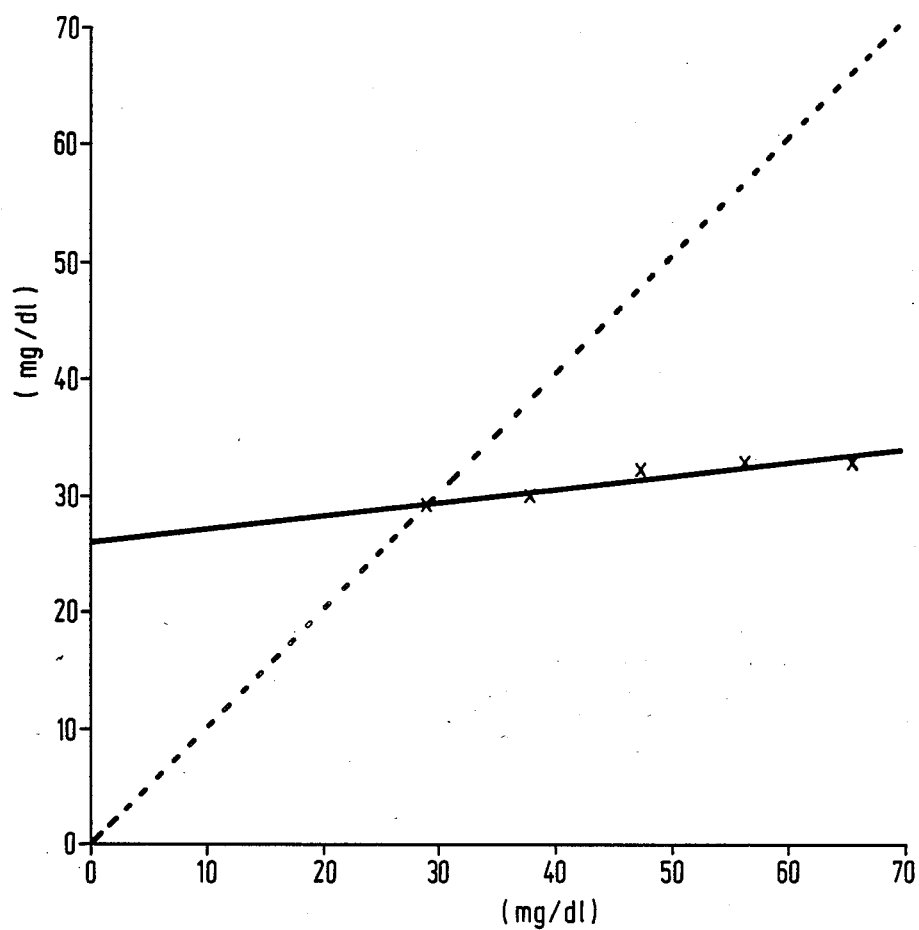
FIG. 2 shows the evaluation of FIG. 1 in the time interval $\Delta t = 0 - 1$ min.
Figure 3:
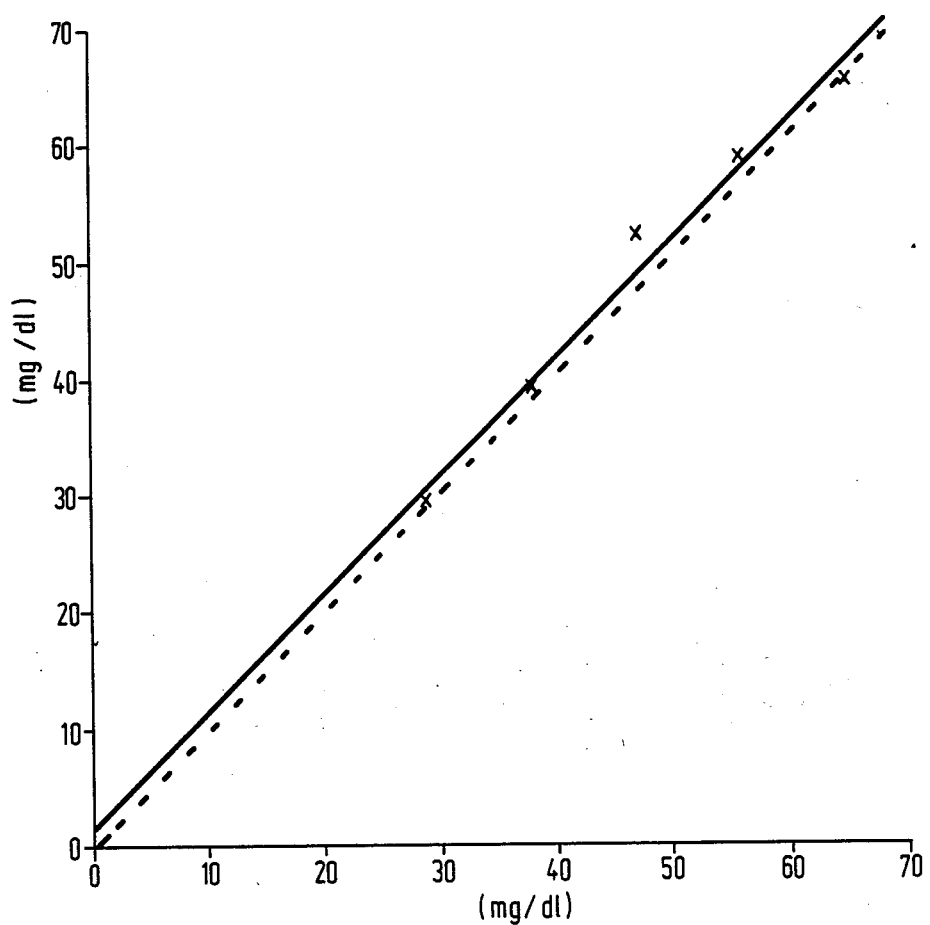
FIG. 3 shows the evaluation of FIG. 1 in the time interval $\Delta t = 5 - 6$ min.

FIG. 1 of the accompanying drawings shows that the extinction increase at 546 nm is initially substantially independent of the HDL cholesterol concentration but, in the further course of the reaction, is clearly dependent thereon. Consequently, the extinction increase during the first minutes is not a measure of the HDL cholesterol concentration (FIG. 2), whereas the extinction increase in the sixth minute is proportional to the HDL cholesterol concentration (FIG. 3).

EXAMPLE 2

Two human sera with the same content of LDL cholesterol but with a different content of HDL cholesterol are mixed in different ratios so that there is obtained a series of samples which contain increasing amounts of HDL cholesterol with a constant LDL cholesterol content. 0.02 ml. amounts of these samples are each incubated at 30° C with 2.0 ml. of a reagent of the following composition:

0.1 M potassium phosphate buffer (pH 6.7)
8.6 mM tribromohydroxybenzoic acid
1.6 mM 4-aminoantipyrine
3 mM sodium cholate
0.1% polyethylene glycol (M.W. 6000)
0.1% THESIT ®
1 U/ml. cholesterol esterase from pig pancreas
1 U/ml. cholesterol oxidase from Brevibacterium
2.5 U/ml. peroxidase As in Example 1, the extinction increase at 546 nm is here initially substantially independent of the HDL cholesterol concentration and in the sixth minute is proportional to the HDL cholesterol concentration.

EXAMPLE 3

Starting from the reaction mixture described in Example 1, the concentrations of the following components are varied: THESIT ®, sodium cholate, cholesterol esterase and cholesterol oxidase. The investigations described in Example 1 are carried out with these variants. The observed dependencies of the HDL concentration are shown in the following Table 1 in the form of the regression data obtained in the case of evaluation of different time intervals:

TABLE 1

| varied material used | favourable measurement interval | correlation coefficient | regression line (x: ther. value mg./dl) |
|---|---|---|---|
| THESIT[R] | | | |
| 0.4 g./l. | 8–10 min. | 0.998 | y = 0.91 + 2.9 |
| 1 g./l. | 4–5 min. | 0.996 | y = 1.22 x − 5.6 |
| 4 g./l. | 2–3 min. | 0.999 | y = 0.68x + 9.4 |
| sodium cholate | | | |
| 1 mmol/l. | 6–10 min. | 0.988 | y = 1.08 x + 0.2 |
| 3 mmol/l. | 4–5 min. | 0.996 | y = 1.22 x − 5.6 |
| 5 mmol/l. | 4–5 min. | 0.997 | y = 0.89 x + 4.9 |
| cholesterol esterase | | | |
| 0.3 U/ml. | 6–7 min. | 0.999 | y = 0.94 x + 1.9 |
| 1 U/ml. | 4–5 min. | 0.996 | y = 1.22 x − 5.6 |
| 3 U/ml. | 4–5 min. | 0.998 | y = 0.98 x − 2.2 |
| cholesterol oxidase | | | |
| 0.3 U/ml. | 5–6 min. | 0.979 | y = 0.93 x + 3.4 |
| 1 U/ml. | 4–5 min. | 0.996 | y = 1.22 x − 5.6 |
| 3 U/ml. | 5–6 min. | 0.996 | y = 1.03 x + 1.7 |

EXAMPLE 4

The reaction mixture contains 0.5 U/ml. cholesterol esterase from Pseudomonas and 2 U/ml. cholesterol oxidase from Streptomyces, otherwise the composition corresponds to that of Example 1. Here, too, there is observed, in the correspondingly selected time intervals, a marked dependency of the HDL cholesterol concentration; in the fourth incubation minute at 37° C., there is obtained, for example, in the case of an evaluation corresponding to FIG 2 or 3, a regression line y=1.02x+1.5 mg./dl. A similar result is also obtained with a combination of 1.5 U/ml. cholesterol esterase from *Candida cylindracea* and 2 U/ml. of cholesterol oxidase from Streptomyces (y=1.13x−0.9).

EXAMPLE 5

The procedure is as explained in Example 1 but, instead of THESIT, there are used other non-ionic detergents. The observed dependencies of the HDL cholesterol concentration are given in the following Table 2 in the form of the regression data obtained in the case of the evaluation at different time intervals.

TABLE 2

| detergent | measurement interval | correlation coefficient | regression line (x = theor. value, mg/dl) |
|---|---|---|---|
| TRITON X 100[R] | | | |
| 1 g./l. | 5–6 min. | 0.991 | y = 0.78 x + 11.2 |
| 2 g./l. | 4–5 min. | 0.993 | y = 0.81 x + 8.9 |
| GENAPOL X80[R] | | | |
| 0.6 g./l. | 6–8 min. | 0.987 | y = 0.95 x − 2.2 |
| 1.5 g./l. | 4–5 min. | 0.995 | y = 0.86 x − 3.6 |

EXAMPLE 6

Figure 4:
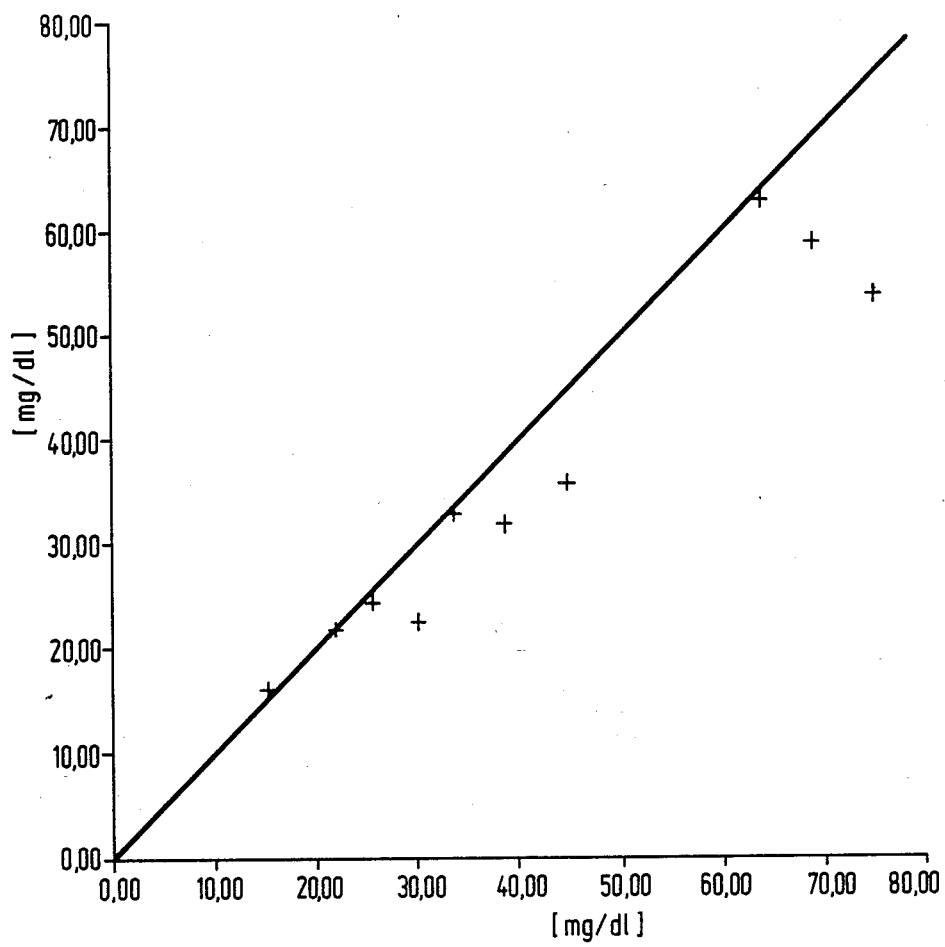
FIG. 4 is a comparison of the HDL cholesterol determination according to the present invention (without the addition of anti-apo-$\beta$-antibodies) with the phosphotungstate precipitation method (PTA)
Figure 5:
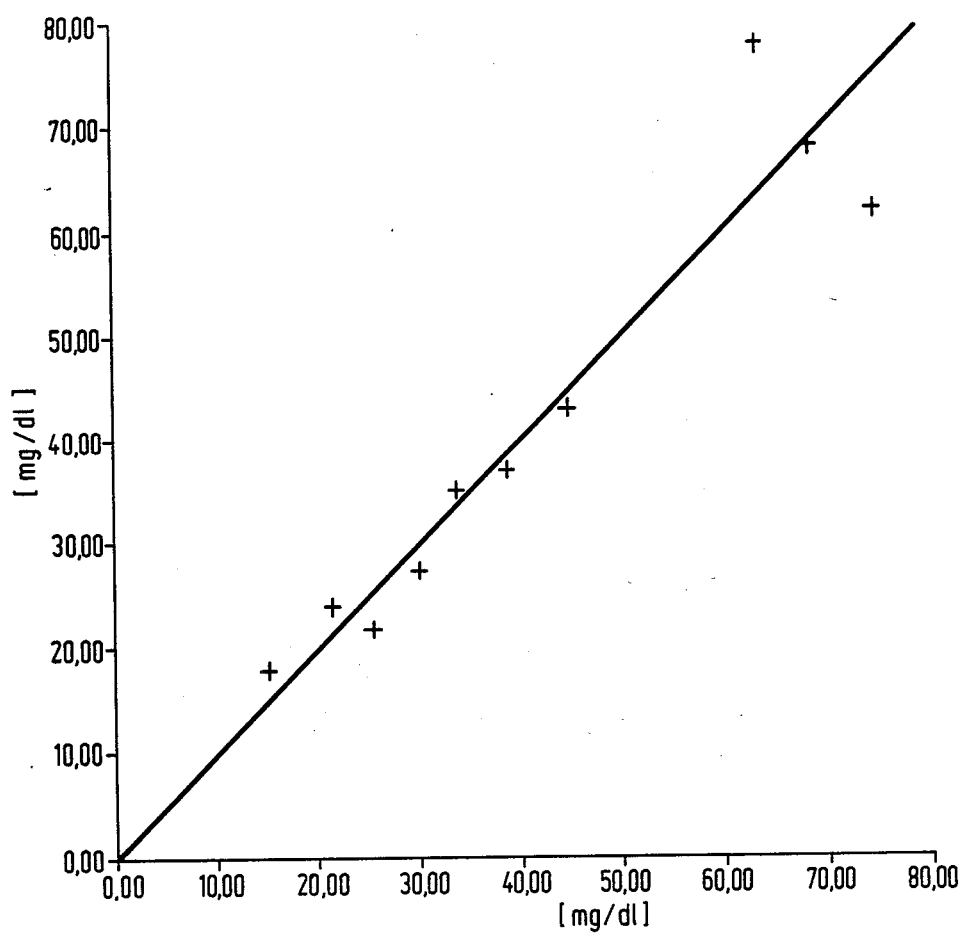
FIG. 5 is a comparison of the HDL cholesterol determination according to the present invention (with the addition of $8 \times 10^{-6}$ mole/liter of anti-apo$\beta$-antibodies) with PTA.

On a photometric automatic analyser, there can be determined the HDL cholesterol content in human sera via the extinction differences in favourably selected time intervals. The calibration takes place by means of a human serum of known HDL cholesterol content. The reagent corresponds, in principle, to the reagent of Example 1, whereby the test can be adapted to the automatic analyser to be used by variation of the activity of cholesterol esterase and/or cholesterol oxidase, of the concentration of sodium cholate and of Thesit, of the time interval, as well as by the addition of commercially available anti-B-antiserum. FIG. 4 of the accompanying drawings shows that, for example, there can be achieved values similar to those which can be achieved with the established phosphotungstic acid precipitation method for HDL cholesterol when the activity of the cholesterol oxidase is reduced in comparison with Example 1 to 0.36 U/ml. and the extinction increase is measured at 30° C. within the seventh minute of the incubation. FIG. 5 of the accompanying drawings shows that, under these conditions, the addition of $8 \times 10^{-6}$ mole/liter of a defatted antibody against LDL still further improves the agreement of the methods. Regression lines (standard main component analysis):

FIG. 4: Y=0.771 x+3.551 (mg./dl.)
FIG. 5: Y=0.981 x+0.034 (mg./dl.)

EXAMPLE 7

The procedure is as described in Example 6. In parallel experiments, independently of one another, the time interval for the photometric measurement and the addition of defatted anti-LDL-antiserum is varied. The comparison of the data obtained for a collective of human sera with the results of the phosphotungstic acid precipitation method is given in the following Table 3 in the form of regression data:

TABLE 3

| concentration Anti-Apo B-IgG | measurement interval | correlation coefficient | regression line (x: PTA precipitation,mg/dl) |
|---|---|---|---|
| $4 \cdot 10^{-6}$ | 3–4 min. | 0.709 | y = 0.44 x + 11.4 |
| | 4–5 min. | 0.829 | y = 0.57 x + 7.9 |
| | 5–6 min. | 0.906 | y = 0.67 x + 3.8 |
| | 6–7 min. | 0.973 | y = 0.77 x + 3.6 |
| | 9–10 min. | 0.826 | y = 0.54 x + 11.3 |
| $8 \cdot 10^{-6}$ | 3–4 min. | 0.684 | y = 0.58 x + 9.8 |
| | 4–5 min. | 0.786 | y = 0.69 x + 4.6 |
| | 5–6 min. | 0.873 | y = 0.84 x + 0.4 |
| | 6–7 min. | 0.968 | y = 0.98 x + 0.03 |
| | 9–10 min. | 0.785 | y = 0.66 x + 6.3 |
| $1.6 \cdot 10^{-5}$ | 3–4 min. | 0.679 | y = 0.55 x + 10.8 |
| | 4–5 min. | 0.770 | y = 0.62 x + 8.3 |
| | 5–6 min. | 0.866 | y = 0.71 x + 5.0 |
| | 6–7 min. | 0.901 | y = 1.04 x + 8.8 |
| | 9–10 min. | 0.757 | y = 0.64 x + 8.8 |

EXAMPLE 8

By suitable choice of the measurement interval, in the case of all measurement temperatures usual in clinical chemistry, there can be achieved a good agreement with the results of the established phosphotungstate precipitation method for HDL cholesterol. For the series of method comparisons given in the following in the form of the regression data on the basis of a collective of 27 human sera, there is used the following embodiment of the process according to the present invention:

apparatus: Hitachi 705
measurement wavelength: 505 nm
comparison wavelength: 600 nm
calibrator: human serum of known HDL cholesterol content
sample volume: 10 μl.
reagent volume: 0.5 ml.
reagent composition:
0 1 M potassium phosphate buffer (pH 6.7)
8.6 mM tribromohydroxybenzoic acid
1.6 mM 4-aminoantipyrine 5 mM sodium cholate
0.1% polyethylene glycol (M.W. 6000)
1.5 g./liter THESIT ® (non-ionic detergent)
0.25 U/ml. cholesterol esterase from pig pancreas cholesterol oxidase as given below
2.5 U/ml. peroxidase The results of the two series a and b are given in the following Tables 4 and 5:

TABLE 4

Series a: 25 U/ml. cholesterol oxidase from *Nocardia*

| temperature | measurement interval | correlation coefficient | regression line (n = 27, X: PTA precipitation) mg/dl |
|---|---|---|---|
| 25° C. | 8–9 min. | 0.954 | y = 0.93 + 4.0 |
|  | 9–10 min. | 0.966 | y = 0.99 + 0.9 |
| 30° C. | 4–5 min. | 0.966 | y = 0.97 x + 0.9 |
|  | 5–6 min. | 0.969 | y = 1.06 x − 2.1 |
| 37° C. | 3–4 min. | 0.961 | y = 1.02 x − 1.3 |
|  | 4–5 min. | 0.896 | y = 1.03 x − 1.1 |

TABLE 5

Series b: 10 U/ml. cholesterol oxidase from *Brevibacterium*

| temperature | measurement interval | correlation coefficient | regression line (n = 27, x: PTA precipitation, mg/dl) |
|---|---|---|---|
| 25° C. | 8–9 min. | 0.807 | y = 0.45 x + 14.6 |
|  | 9–10 min. | 0.858 | y = 0.52 x + 13.2 |
| 30° C. | 7–8 min. | 0.937 | y = 0.93 x + 4.1 |
|  | 8–9 min. | 0.938 | y = 0.88 x + 4.0 |
| 37° C. | 3–4 min. | 0.929 | y = 0.87 x + 6.4 |
|  | 4–5 min. | 0.914 | y = 0.74 x + 9.5 |

We claim:

1. Process for specific determination of HDL cholesterol in a serum lipoprotein containing sample which contains LDL comprising adding to said sample pancreatic cholesterol esterase to liberate cholesterol from cholesterol esters, cholesterol oxidase and oxygen to oxidize said liberated cholesterol with the formation of hydrogen peroxide and kinetically measuring one of hydrogen peroxide formation or oxygen consumption, within 2–15 minutes thereafter as a measurement of HDL cholesterol, said measuring and reaction taking place at a temperature of from 20° C to 40° C during a predetermined time interval during which measurement one maintains a pancreatic cholesterol esterase concentration of from 0.05 to 30 U/ml, a cholesterol oxidase concentration of from 0.1 to 50 U/ml, a tenside of a bile acid group at a concentration of from 1.0 to 20 mMole/liter, concentration of a non-ionic detergent of from 0.1 to 10g/liter and a pH of from 5 to 9.

2. Process according to claim 1, comprising adding the non-ionic detergent after the addition of the oxidase to said sample but from 1 to 14 minutes before said kinetic measurement.

3. Process according to claim 1, comprising carrying out the kinetic measurement within 3 to 5 minutes after addition of the cholesterol oxidase.

4. Process according to claim 1, comprising maintaining a pancreatic cholesterol esterase concentration of from 0.05 to 10 U/ml.

5. Process according to claim 1 comprising maintaining a cholesterol oxidase concentration of from 1 to 30 U/ml.

6. Process according to claim 1 comprising maintaining a concentration of tenside of from 1.5 to 8 mMole/liter.

7. Process according to claim 1 comprising maintaining a concentration of non-ionic detergent of from 0.4 to 4g/liter.

8. Process according to claim 1, comprising carrying out said measurement at a temperature of from 25° C to 37° C.

9. Process according to claim 1, wherein said tenside is sodium cholate.

10. Process according to claim 1 wherein said non-ionic detergent is a polyethylene oxide group containing detergent.

11. Process according to claim 1, further comprising carrying out said process in the presence of at least one of anti-LDL-antibodies and antiapolipoprotein B antibodies.

12. Process according to claim 1, further comprising determining LDL cholesterol within 2 minutes after addition of the cholesterol oxidase by determining hydrogen peroxide formation kinetically.

13. Process according to claim 1, further comprising adding an amount of at least one of detergent and pancreatic cholesterol esterase sufficient to oxidise total cholesterol contained in the sample to form hydrogen peroxide and determining an end value of a color forming reaction as a measure of the total cholesterol content of the sample.

14. Reagent for specific determination of HDL cholesterol in a serum lipoprotein containing sample which contains LDL comprising pancreatic cholesterol esterase, cholesterol oxidase, a tenside of a bile acid group, a non-ionic detergent, a buffer at pH from 5 to 9, and a system for photometric determination of hydrogen peroxide, wherein said reagent contains cholesterol esterase in a concentration of from 0.05 to 30 U/ml., cholesterol oxidase in a concentration of from 0.1 to 50 U/ml., tenside of the bile acid group in a concentration of from 1.5 to 8m Mole/liter and non-ionic detergent in a concentration of from 0.1 to 10g/liter.

15. Reagent according to claim 14 further comprising at least one of antibodies against LDL and antibodies against apolipoprotein B.

16. Reagent according to claim 14 wherein said reagent is impregnated in or on a carrier material.

17. Reagent according to claim 16, wherein the carrier material is an absorbent, swellable or film-forming material.

* * * * *